US006603547B2

(12) United States Patent
Moersen et al.

(10) Patent No.: US 6,603,547 B2
(45) Date of Patent: Aug. 5, 2003

(54) METHOD FOR DETERMINATION OF THE RADIATION STABILITY OF CRYSTALS

(75) Inventors: Ewald Moersen, Mainz (DE); Burkhard Speit, Jena (DE); Lorenz Strenge, Ingelheim (DE); Joerg Kandler, Jena (DE)

(73) Assignee: Schott Glas, Mainz (DE)

( * ) Notice: Subject to any disclaimer, the term of this patent is extended or adjusted under 35 U.S.C. 154(b) by 96 days.

(21) Appl. No.: 09/975,173

(22) Filed: Oct. 11, 2001

(65) Prior Publication Data

US 2002/0105643 A1 Aug. 8, 2002

(30) Foreign Application Priority Data

Oct. 11, 2000 (DE) .......................................... 100 50 349

(51) Int. Cl.$^7$ .................................................. G01J 3/30
(52) U.S. Cl. ........................... 356/318; 356/319; 356/30
(58) Field of Search ................................. 356/318, 326, 356/432, 30, 300–334

(56) References Cited

U.S. PATENT DOCUMENTS

| 3,269,847 | A |   | 8/1966  | Cohen |
|---|---|---|---|---|
| 5,314,831 | A | * | 5/1994  | Hirae et al. ..................... 437/8 |
| 5,774,213 | A | * | 6/1998  | Trebina et al. ............... 356/320 |
| 5,835,200 | A | * | 11/1998 | Smith et al. ................... 356/30 |
| 5,841,532 | A | * | 11/1998 | Yoshida et al. ............. 356/318 |
| 5,991,021 | A | * | 11/1999 | Mukherjee et al. ......... 356/317 |
| 6,515,738 | B1 | * | 2/2003 | Barnes et al. ................. 356/30 |

FOREIGN PATENT DOCUMENTS

| DE | 196 32 349 C1 | 1/1998 |
|---|---|---|
| EP | 0 875 778 A | 11/1998 |
| EP | 0 938 030 A | 8/1999 |
| WO | 98 07053 A | 2/1998 |

OTHER PUBLICATIONS

Arbuzov et al: "Study of the Thermally Stimulated Glass . . . " Journal of Non–Crystalline Solids, North–Holland Publishing Company, Amsterdam, NL, Bd. 231, Nr. 1–2, Jul. 1, 1998, pp. 125–133.
H. Imai et al: "Generation of E'Center . . . " Phys. Rev. B, Bd. 48, Nr. 5, Aug. 1, 1993, pp. 3116–3123.

(List continued on next page.)

Primary Examiner—Michael P. Stafira
Assistant Examiner—Willie Davis
(74) Attorney, Agent, or Firm—Michael J. Striker

(57) ABSTRACT

The method for determining radiation stability of a crystal to radiation of a working wavelength to be employed in a subsequent application includes taking a first absorption spectrum (A) of a cleaved piece of the crystal with a given thickness (D) over a predetermined wavelength range from a first wavelength ($\lambda_1$) to a second wavelength ($\lambda_2$) by means of a spectrophotometer. Then the cleaved piece of the crystal is irradiated with an energetic radiation source so as to form all theoretically possible color centers (saturation). After the irradiating a second absorption spectrum (B) of the cleaved piece of crystal is taken over the same predetermined wavelength range. Then a surface integral of a difference spectrum of the first absorption spectrum and the second absorption spectrum over the predetermined wavelength range is formed and divided by the thickness (D) to obtain a scaled surface integral value. The absorption coefficient $\Delta k$ at the working wavelength for the subsequent application is then obtained preferably from the scaled surface integral value for the damage induced by the energetic radiation and a calibration curve relating the absorption coefficient at the working wavelength to the surface integral of the absorption coefficient induced by the energetic radiation.

14 Claims, 1 Drawing Sheet

OTHER PUBLICATIONS

Hosono H et al: "Interaction of F2 Excimer Laser With . . ." Muclear Instruments & Methods in Physics Research, Section–B: Beam Interactions with Materials and Atoms, North–Holland Publishing Company, Amsterdam, NL, BD. 166–167, May 2000, pp. 691–697.

Karlitschek P et al: "Influence of Hydrogen on the Colour Center . . ." Optics Communications, North–Holland Publishing Co, Amserdam, NL, Bd. 155, Nr. 4–6, Oct. 15, 1998, pp. 376–385.

SU 1755127 A1, WPIDS–Abstract 1993–263623 [33], Derwent Information Ltd.

K.R. Mann et al: "Characterizing the Absorption and Aging . . . ". SPIE, vol. 3334, p. 1055.

I. Toepke and D. Cope: "Improvements in Crystal Optics for Excimer Laser . . . ", SPIE vol. 1835, Excimer Lasers 1992, pp. 89–97.

K.–Th. Wilke and J. Bohm "Kristallzuechtung", Verlag Harri Deutsch, Thun, Frankfurt/Main 1988, pp. 671–701.

* cited by examiner

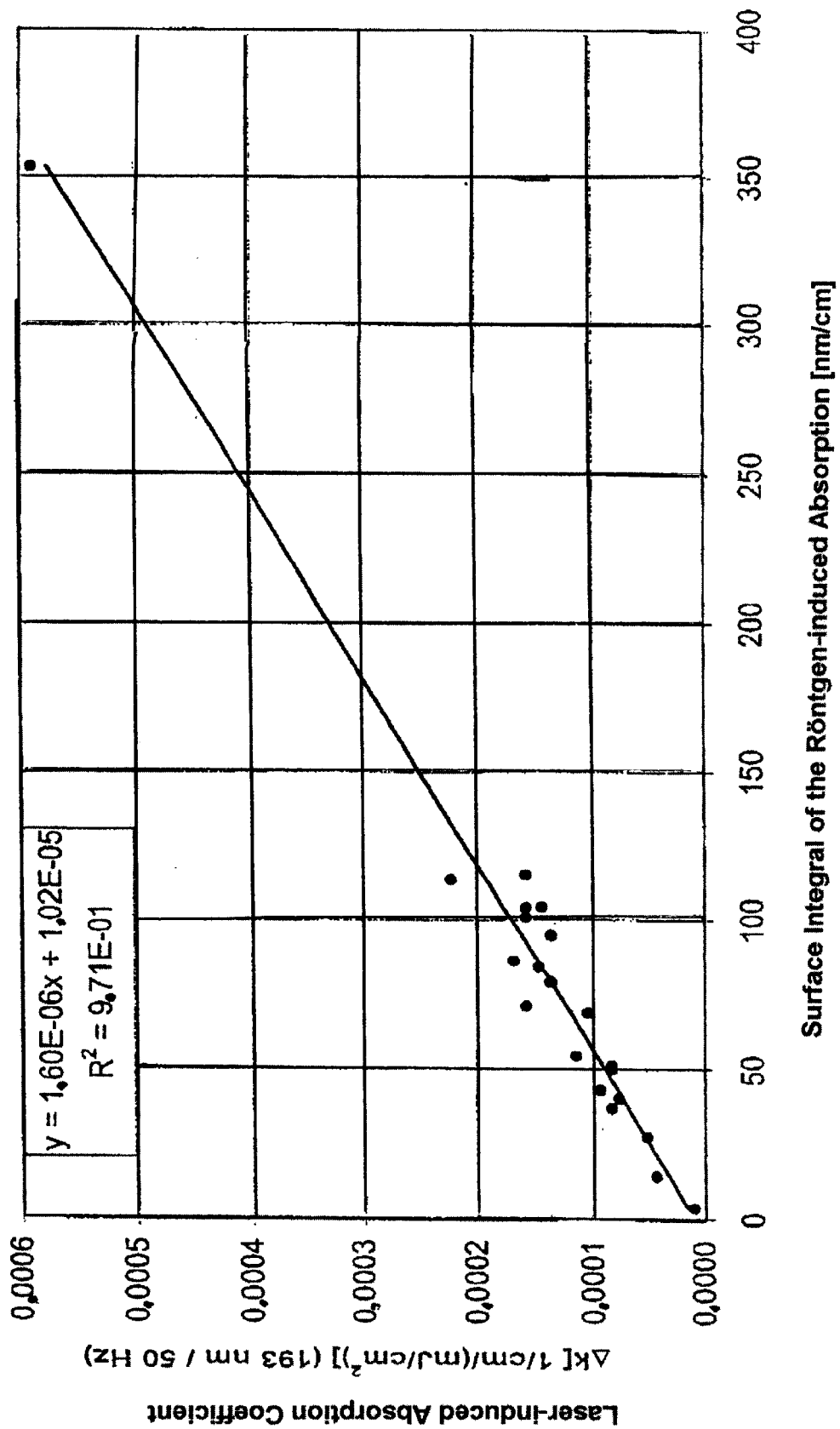

METHOD FOR DETERMINATION OF THE RADIATION STABILITY OF CRYSTALS

BACKGROUND OF THE INVENTION

The present invention relates to methods of determination of radiation stability of crystals, especially of crystals for optical elements, such as lenses, and to the use of crystals of a given radiation stability for manufacture of optical components and electronic units.

It has been shown that color centers arise in crystals at crystal defects cause by the presence of foreign atoms and at crystal lattice imperfections due to irradiation of the crystals. This means that the more light or electromagnetic radiation that is propagated in a crystal, the greater the number of color centers formed in the crystal. Because of this the light absorption of the crystal increases or the light transmittance decreases. The formation of color centers and the decrease in radiation transmission caused by that increase has proven troublesome or problematic, especially in optical components, through which energetic light, such as laser light, is conducted, as in steppers, with which structures of integrated circuits are optically projected on a photo-lacquer-coated wafer.

This formation of color centers plays an important role in optical structuring by lasers. It has already been attempted to make crystals of sufficient perfection and sufficient purity so that they are nearly free of foreign atoms and filter defects. However since impurities of less than 1 ppm in optical components, especially those used for DUV (Deep Ultra Violet, $\lambda < 250$ nm), already cause notable difficulties, each individual crystal must be tested for radiation stability prior to use in an optical component. The procedure up to now has been to cut a sample with a length of about 1 to 10 cm and a cross-section of about 2.5 cm×2.5 cm of the crystal to be tested. Subsequently the front face of the sample was finely polished and irradiated by means of a laser, usually with a working wavelength of 157 nm generated by an $F_2$ excimer laser and/or with a current working wavelength for a stepper of 193 nm generated by an ArF excimer laser. The usual energy density amounts to from 1 to 100 mJ/cm$^2$ with a pulse frequency of 50 to 500 Hz and a pulse rate of $10^4$ to $10^7$. The absorption of the sample before and after laser irradiation at the respective working wavelengths was measured with a spectrophotometer. The laser-induced transmission decrease was calculated at both values. The conversion to the absorption coefficient was then performed by calculation according to the method described by K. R. Mann and E. Eva in "Characterizing the absorption and aging behavior of DUV Optical Material by High-resolution Excimer Laser Calorimetry", SPIE, Vol. 3334, p. 1055.

The position can then be determined, which the optical elements made with the crystalline material can take, because of the established radiation resistance or stability. The energy density of the light irradiated into the optics is different at the respective application wavelengths at the different positions. Only those crystals may be used, which have high radiation stability, for the optical elements that are furthest to the outside, i.e. toward the radiation source. Also those optical elements in which the laser radiation is focused must have high radiation stability. The formation of many color centers leads furthermore to a higher absorption, i.e. that is more radiation energy is absorbed in the crystal. This has the consequence that the crystalline material and thus the optical lens are heated, whereby the refractive index and thus the imaging properties change. The higher the radiation stability, the less energy is converted into heat in the lens system.

To perform this testing process a high capacity of expensive excimer lasers must be provided, which requires great maintenance work.

The time interval between removing the crude crystals from the crystal growing vessel and establishing their suitability for a particular application, which presupposes high radiation stability, is thus extremely large because of the work-intensive preparation of the samples. That also means that not only is there a high material consumption, but also an additional expensive storage is required for the large crude crystals prior to the material allocation.

The build-up of color centers in optical materials by means of a cobalt source at a 1 megarad dosage is described by I. Toepke and D. Cope in "Improvements in Crystal Optics For Excimer Laser", SPIE Vol. 1835 Excimer Lasers (1992), pp. 89 to 97. The radiation damage resulting therefrom was found to be well correlated with that produced by an excimer laser.

This method has the disadvantage that the stringent regulations for use of highly radioactive material must be considered, so that it is not suitable as a practical method.

Also this measurement method consumes a large amount of expensively grown crystalline material, whereby the total yield of the grown crystals is further reduced. Furthermore the crystalline samples must be prepared in a costly and time-consuming process by means of sawing and polishing the measured portion of them.

SUMMARY OF THE INVENTION

It is an object of the present invention to provide a rapid and economical method for reliable determination of the radiation stability of crystals, which is performed by simple inexpensive means without great loss of material.

According to the invention the resistance or stability of crystals to intense radiation at an arbitrary wavelength can be determined with any undefined and untreated crystal or a cleaved piece from it, when the surface integral of the difference spectrum formed from respective spectra taken prior to and after irradiation over a fixed wavelength range from a first wavelength $\lambda_1$ to a second wavelength $\lambda_2$ is calculated.

This procedure usual comprises measuring a first transmission spectrum (spectrum A) over an arbitrarily predetermined wavelength range from a first wavelength $\lambda_1$ to a second wavelength $\lambda_2$ and then stimulating or exciting the crystal, preferably with short-wave energetic radiation and preferably so that all or nearly all the theoretically possible color centers have been formed. After that a second transmission spectrum (spectrum B) of the crystal is measured in the same wavelength range from the first wavelength $\lambda_1$ to the second wavelength $\lambda_2$. It has now been shown that the difference of the surface integrals from the first wavelength $\lambda_1$ to the second wavelength $\lambda_2$ of the transmission curve before and after irradiation is a measure of the radiation resistance or stability and is linearly related to the maximum change in the absorption coefficient $\Delta k$ to be expected. The spectra are preferably taken with a spectrophotometer. Furthermore it has proven satisfactory to scale the spectrum in relation to the thickness of the crystal (length of the light path through the crystal).

This result is thus surprising, because the absorption or transmission spectrum for each individual crystal should be different, since different impurities and crystal defects produce it.

It is possible to prepare a calibration curve, when, as described above, the surface integral of the difference spectrum is determined and compared with or plotted versus the radiation damage measured with conventional methods for the same crystal. For example, the method as described by K. R. Mann and E. Eva, in "Characterizing the absorption and aging behavior of DUV Optical Material by High-resolution Excimer Laser Calorimetry", SPIE, Vol. 3334, p. 1055, may be used as the conventional method. A linear calibration curve is obtained from the measured values. It is possible to eliminate the color centers formed in the conventional method by gentle heating, so that the measurement can be performed with the same crystal. It is of course possible to measure the calibration curve with the aid of a few pairs of values, however because of laser instabilities it is particularly preferred to determine the calibration curves of crystals of differing purity and/or radiation resistances. A measured calibration curve is specific for the given crystalline material. For example, when the calibration curve for a $CaF_2$ crystal is measured, it will be the same for all $CaF_2$ crystals; however the calibration curve, for example, for $BaF_2$ differs from it.

Thus the radiation damage for a crystal is produced in conventional methods, preferably with those wavelengths, which also should be used in optical elements that are made later using the crystal. The radiation damage values obtained are then plotted versus the surface integral of the difference spectrum obtained by the method according to the invention to form a calibration curve. Suitable radiation sources for performing the induced absorption according to the invention are Röntgen radiation sources and other energetic radiation sources, such as radioactive sources, e.g. $Co^{60}$. However Röntgen radiation sources are particularly preferred according to their invention because they are easy to handle, readily available and economical.

The coloring (radiation damage) produced by means of Röntgen radiation sources is surprisingly different from the known classical laser damage. The crystal coloring produced by laser damage has a half life of about one day at room temperature, i.e. the original color returns comparatively rapidly, while the color produced by Röntgen radiation remains the same after storage for about a month in the dark.

An additional important difference between the radiation damage produced by Röntgen radiation sources and that produced by laser radiation is that it may be rapidly relaxed by means of irradiation with laser light of the same wavelength but reduced energy.

The energy density required for performing the method according to the invention is variable over a wide range and depends only on the time interval for saturation to be reached. Usually however an energy density of $10^3$ to $10^5$ Gy, preferably $5 \times 10^3$ to $5 \times 10^4$ Gy, is used. The irradiation time interval required to obtain saturation usually amounts to, e.g., 10 to 360 minutes, preferably from 30 to 180 minutes. A second irradiation experiment can be performed according to the invention and the intensities of the absorption bands and/or the absorption spectra can be compared with each other in order to control the saturation. When no change in absorption intensity is found after both irradiation experiments, the desired saturation condition for the irradiation has been reached.

The value of the surface integral of the difference spectrum according to the invention or the difference of the surface integrals of the absorption or transmission spectra before and after irradiation is of course dependent on the selected wavelength range. When this arbitrarily selected range is established, then this area is a measure of the radiation damage for the particular material being studied.

The fixed wavelength range of from a first wavelength ($\lambda_1$) to a second wavelength ($\lambda_2$), in which the absorption spectrum is measured, preferably includes the working wavelength of the optical element used in the later application. However it has been shown that the working wavelength can be outside of the fixed wavelength range. However the working wavelength should not be far from the fixed wavelength range.

In order to guarantee that all color centers are actually produced in the crystal, the thickness of the irradiated crystal, or the cleaved piece of the crystal, should not be too large. Otherwise with greater crystal thickness, a uniform exposure of the bulk of the crystalline material is not guaranteed according to the stability of the crystal. This is due to the fact that a larger part of the radiation falling on the crystal is absorbed along a first part of the path of the radiation through the crystal in the case of the greater crystal thickness. This would lead to differences between the formation of color centers at the crystal surface and in the bulk of the crystal through which the radiation passes.

Respective radiation conditions should be selected, at which all color centers are excited or formed. If the spectrum prior to irradiation is compared with the spectrum after radiation, its difference directly reproduces a saturation state and shows the absorption with the maximum intensity at the selected wavelength range, which can be produced during irradiation with wavelengths used during the later application.

A great advantage of the invention is that the cleaved piece of the crystal does not require polishing nor does its thickness need to be accurately measured. Thus an arbitrary cleaved piece of crystal can be used. Since crystals can usually be fractured or broken along their crystal axes, parallel surfaces are always available for measurement of the absorption spectra in a spectrophotomer. The distances of the surfaces from each other, i.e. the thickness of the crystal, or the path length for the light passing through it, can be conveniently measured with the aid of a micrometer screw or sliding gauge. The light beam of the spectrophotometer for determination of the absorption or the radiation damage is preferably perpendicular to the crystal surfaces.

The difference between both absorption measurements prior to the first irradiation A and after the second irradiation B respectively gives the difference spectrum, with which the radiation stability or damage of the crystal is determined. The maximum absorption coefficient ($\Delta k$) (1/cm) can be calculated without more according to the Lambert-Beer Law over the known thickness of the cleaved piece of the crystal. To obtain a calibration curve then the absorption coefficient $\Delta k$ is plotted versus the wavelength in the difference spectrum. The area under the difference spectrum is indicated in the following as the surface integral of the Röntgen induced absorption. First by forming the difference spectrum it is possible to use a completely unprocessed crystal or cleaved piece of crystal, whose surfaces are not defined, since the influence of the surface is eliminated. Furthermore the effect of the absorption bands, which are present in the crystal and which relate to the irradiation and the impurities (so-called initial absorption), is eliminated.

The method according to the invention is universally suitable for all crystals. However it is especially suitable for fluoride crystals, especially alkali fluorides and alkaline earth fluorides, particularly $LiF_2$, $CaF_2$ and $BaF_2$.

The preferred working wavelengths used in the later applications are those of lasers, especially of excimer lasers, such as ArF excimer lasers and $F_2$ excimer lasers, namely 193 nm and 157 nm.

For verification of the method according to the invention conventional sample bodies (measurement bars) were prepared for irradiation with the light of an excimer laser, from crystals from which the cleaved piece was cut for the Röntgen experiments. The measurement bars were taken from the same piece of raw crystal, from which the cleaved piece was taken. The measurement bars were cut to a length of 10 cm and a cross-section of 2.5 cm×2.5 cm. Subsequently the front faces were polished.

The laser radiation used to irradiate the crystal had an energy density of 1 to 20 mJ/cm² and was produced with an excimer laser at a pulse frequency of 50 to 500 Hz with a pulse count of $10^4$ to $10^7$. The change of the absorption coefficient Δk was determined from the difference between the absorption before and after the laser irradiation at the application wavelength. This change of the absorption is designated in the following as the laser-induced change of the absorption coefficient Δk.

It was surprisingly found according to the invention that there was a linear correlation between the laser-induced change of the absorption coefficient Δk, for example, at the above-described excimer laser wavelengths of 193 and 157 nm, and the surface integral normalized to the crystal piece thickness of the Röntgen-induced absorption, especially in the wavelength range from 190 nm to 1000 nm. The correlation results when the pairs of values from the laser-induced change of the absorption coefficient Δk and the surface integral of the Röntgen-induced absorption per crystal thickness, which result from the measurements with the laser rods and the cleaved piece of the same crystal, are plotted for different crystalline samples. Moreover the values of the laser-induced change of the absorption coefficient Δk are normalized to the energy density 1 mJ/cm². This calculation is possible since a linear correlation between the laser-induced absorption coefficient Δk and the radiation energy density exists at the application wavelength; especially with samples, which are made from synthetic raw material.

The same experiments were performed using gamma radiation with $Co^{60}$ instead of Röntgen radiation. The radiation conditions for the gamma radiation were selected so that saturation conditions were again used. The gamma radiation experiments have the same results as the Röntgen radiation experiments. However the hard radiation from the $Co^{60}$ is substantially more expensive in operation.

The above-described linear correlation shows that the measurement of the surface integral of the Röntgen-induced absorption provides a measure of the radiation stability to be expected on irradiation with an excimer laser. Simultaneously the plotting of the laser-induced change of the absorption coefficient Δk versus the surface integral of the Röntgen-induced absorption give the ratio of the laser-induced change of the absorption coefficient Δk versus the surface integral so that an absolute statement regarding the expected laser stability is possible by measuring the surface integral.

The crystals obtained by the method according to the invention are suitable for use in and for making optical lenses, steppers, wafers, electronic components, especially chips and computers, as well as micromechanical devices.

The following examples should illustrate the invention in greater detail, without limiting the appended claims.

BRIEF DESCRIPTION OF THE DRAWING

The objects, features and advantages of the invention will now be illustrated in more detail with the aid of the following description of the preferred embodiments, with reference to the accompanying sole FIGURE which is a graphical illustration of a correlation of laser-induced damage caused by an ArF excimer laser and Röntgen damage.

DETAILED DESCRIPTION OF THE INVENTION

The crystals tested were made according to the Bridgeman-Stockbarger Method. For example synthetic $CaF_2$ powder was filled in a vessel. The powder was melted at a temperature of from 1400 to 1460° C. Crystals were drawn into a temperature field by lowering of the vessel. The crystal growth occurred under a vacuum of $10^{-4}$ to $10^{-5}$ Torr.

Other known crystal growing processes, such as the Czochralski and the Nacken-Kyropoulus Process, which are generally for the commercial growth of $CaF_2$ crystals, have no or only a subordinate importance here (Lit.: K. -Th. Wilke and J. Bohm, "Crystal Growth", Verlag Harri Deutsch, Thun, Frankfurt/Main 1998).

The crystalline $CaF_2$ is cleaved along the {1,1,1}-direction of the crystal, in contrast to amorphous quartz glass, which is also used for optical components in DUV photolithography.

Cleaved pieces could be separated from the raw crystals. For example, this would be performed at the bottom of the crystal. The bottom would be cleaved from the remained of the crystal. A piece was prepared by cleavage from the bottom. The cleaved piece so obtained had a thickness D of from 0.4 to 0.5 cm. The cleaved piece was put in a double beam spectrophotometer and the absorption along the thickness D was measured (measurement A). The wavelength range employed was from 190 nm to 1000 nm.

The cleaved piece was now put in an apparatus for Röntgen irradiation and adjusted. The cleaved piece was irradiated with an energy of 80 to 150 KeV (Dosage $10^4$ Gy), so that all the color centers that were sensitive to Röntgen radiation were produced or excited (saturation). The irradiation occurred in the direction of the thickness D.

The cleaved piece was then again placed in the spectrophotometer (same measurement spot). The absorption spectra in a wavelength range from 190 nm to 1000 nm was measured (measurement B) after a fixed time interval from the irradiation (here 2 hr). The change of the absorption was calculated from the difference of the measured spectra for measurements A and B. The change of the absorption coefficient Δk [1/cm] could be calculated by including the known thickness D. This change of absorption coefficient was then plotted versus the wavelength λ[nm]. The surface integral could now be calculated from this plot.

A measurement bar very close to the cleaved piece was cut with a length L×width×height of 100 mm×25 mm×25 mm from the remaining bottom piece of the crystal. The measurement bar was polished on its front face in order to minimize the scattering effect for the laser radiation at its surface. The absorption coefficients k [1/cm] before and after irradiation with an excimer laser were determined in a direction of the length L of this measurement bar. The difference Δk was calculated from both values of k. The application wavelength was 193 nm (for the ArF excimer laser) and 157 nm ($F_2$ excimer laser). The measurements were performed for different crystals that were grown. The values are tabulated in Table 1.

TABLE I

DISCOLORATION OF A CALCIUM FLUORIDE CRYSTAL INDUCED BY RÖNTGEN RADIATION

| SURFACE INTEGRAL OF THE RÖNTGEN-INDUCED ABSORPTION [nm/cm] | LASER-INDUCED ABSORPTION COEFFICIENT $\Delta k$ [1/cm/mJ/cm$^2$] (193 nm/50 Hz) |
|---|---|
| 113.29 | 0.00022 |
| 104.29 | 0.00016 |
| 353.30 | 0.00059 |
| 86.10 | 0.00017 |
| 40.28 | 0.00008 |
| 115.03 | 0.00016 |
| 101.00 | 0.00016 |
| 71.00 | 0.00016 |
| 54.70 | 0.00012 |
| 51.54 | 0.00008 |
| 43.00 | 0.00009 |
| 104.66 | 0.00014 |
| 37.06 | 0.00008 |
| 27.50 | 0.00005 |
| 84.06 | 0.00015 |
| 79.00 | 0.00014 |
| 79.30 | 0.00014 |
| 68.62 | 0.00011 |
| 94.45 | 0.00014 |
| 50.10 | 0.00008 |
| 3.90 | 0.00001 |
| 14.32 | 0.00004 |
| 27.98 | 0.00013 |
| 28.10 | 0.00012 |

A plot or graphical illustration of pairs of values of the laser-induced change of the absorption coefficient $\Delta k$ and the surface integral of the Röntgen-induced absorption was a straight line. In other words, there was a linear correlation between the laser-induced change of the absorption coefficient $\Delta k$ and the surface integral of the Röntgen-induced absorption as shown in the sole FIGURE. The scatter of the values is substantially the result of energy stability problems with the ArF excimer laser.

A formula, from which the laser-induced change in the absorption coefficient $\Delta k$ can be calculated given the surface integral of the Röntgen-induced absorption F1, may be calculated by linear regression analysis from the correlation plotted in the sole FIGURE. This formula is $$\Delta k[1/cm] = 1.60E{-}6 * F1[nm/cm] + 1.02E{-}5.$$

This functional relationship is essentially a calibration curve and permits rapid calculation of the laser-induced absorption coefficient from the difference spectra, after Röntgen-irradiation in units of [1/cm/(mJ/cm$^2$)]. The wavelength range, over which the integration takes place, extends for this calibration curve from 190 nm to 1000 nm (sole FIGURE).

The calibration curve is essential, when the user tests an optical material for the laser-induced change of the absorption coefficient $\Delta k$ at the working wavelength for a given application. Other linear correlations or dependencies, which could be easily determined by one skilled in the art, would result at other laser wavelengths (i.e. alternative working wavelengths).

Comparable linear correlations are found, when as in the indicated case the integration takes place over other wavelength ranges. Also it is possible to call upon the intensities of individual absorption bands for the linear connection or correlation after the Röntgen-induced color change or absorption change.

The disclosure in German Patent Application 100 50 349.7 of Oct. 11, 2000 is incorporated here by reference.

This German Patent Application describes the invention described hereinabove and claimed in the claims appended hereinbelow and provides the basis for a claim of priority for the instant invention under 35 U.S.C. 119.

While the invention has been illustrated and described as embodied in a method for determination of the radiation stability of a crystal, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method for determining radiation stability of a crystal to radiation of a working wavelength to be employed in a subsequent application, said method comprising the steps of:
   a) measuring a first absorption spectrum (A) of said crystal, or a cleaved piece of said crystal, of a given thickness (D) over a predetermined wavelength range from a first wavelength ($\lambda_1$) to a second wavelength ($\lambda_2$) by means of a spectrophotometer;
   b) after the measuring of step a), irradiating said crystal, or said cleaved piece of said crystal, with an energetic radiation source with an energy density sufficiently high to form color centers under saturation conditions for a predetermined irradiation time interval;
   c) after the irradiating of step b), measuring a second absorption spectrum (B) of said crystal or said cleaved piece of said crystal over said predetermined wavelength range from said first wavelength ($\lambda_1$) to said second wavelength ($\lambda_2$);
   d) forming a surface integral of a difference spectrum of said first absorption spectrum and said second absorption spectrum over said predetermined wavelength range from said first wavelength ($\lambda_1$) to said second wavelength ($\lambda_2$) and dividing said surface integral by said thickness to obtain a value of said surface integral per unit thickness; and then
   e) determining an absorption coefficient ($\Delta k$) at said working wavelength from said value of said surface integral per unit thickness.

2. The method as defined in claim 1, wherein said energetic radiation source is a Röntgen radiation source or a Co$^{60}$ radiation source.

3. The method as defined in claim 1, wherein said cleaved piece of said crystal has a thickness of less than 10 mm.

4. The method as defined in claim 3, wherein said thickness is less than 5 mm.

5. The method as defined in claim 1, wherein said crystal is a fluoride crystal.

6. The method as defined in claim 1, wherein said crystal is a CaF$_2$ crystal, a BaF$_2$ crystal or a LiF crystal.

7. The method as defined in claim 1, wherein said working wavelength is 193 nm or 157 nm.

8. The method as defined in claim 1, wherein said energy density is from 10$^3$ to 10$^5$ Gy.

9. The method as defined in claim 1, wherein said predetermined irradiation time interval is from 10 to 360 minutes.

10. The method as defined in claim 1, wherein said predetermined wavelength range includes said working wavelength.

11. The method as defined in claim 1, further comprising providing a calibration curve, said calibration curve consisting of a plot of measured absorption coefficients ($\Delta k$) before and after irradiation at said working wavelength versus normalized values of surface integrals of difference spectra before and after irradiation with said energetic radiation source for a plurality of crystal samples having an identical chemical composition to that of said crystal and obtaining said absorption coefficient ($\Delta k$) for said crystal from said calibration curve and said value of said surface integral per unit thickness.

12. The method as defined in claim 11, wherein said crystal and said crystal samples are fluorides, said energetic radiation source is a Röntgen radiation source and said predetermined irradiation time interval is from 10 to 360 minutes.

13. The method as defined in claim 12, wherein said working wavelength is 193 nm or 157 nm and said working wavelength is produced by means of an excimer laser.

14. A process for making an optical lens, stepper, wafer, electronic component or micromechanical apparatus with a crystal having a predetermined radiation stability at a working wavelength for said optical lens, said stepper, said wafer, said electronic component or said micromechanical apparatus, wherein said process comprises determining said predetermined radiation stability of said crystal at said working wavelength by means of a testing method, said testing method comprising the steps of:

a) measuring a first absorption spectrum (A) of said crystal, or a cleaved piece of said crystal, of a given thickness (D) over a predetermined wavelength range from a first wavelength ($\lambda_1$) to a second wavelength ($\lambda_2$) by means of a spectrophotometer;

b) after the measuring of step a), irradiating said crystal, or said cleaved piece of said crystal, with an energetic radiation source with an energy density sufficiently high to form color centers under saturation conditions for a predetermined irradiation time interval;

c) after the irradiating of step b), measuring a second absorption spectrum (B) of said crystal, or said cleaved piece of said crystal, after said irradiating over said predetermined wavelength range from said first wavelength ($\lambda_1$) to said second wavelength ($\lambda_2$);

d) forming a surface integral of a difference spectrum of said first absorption spectrum and said second absorption spectrum over said predetermined wavelength range from said first wavelength ($\lambda_1$) to said second wavelength ($\lambda_2$) and dividing said surface integral by said thickness to obtain a value of said surface integral per unit thickness; and then e) determining an absorption coefficient ($\Delta k$) at said working wavelength from said value of said surface integral per unit thickness.

\* \* \* \* \*